United States Patent
O'Lenick, Jr.

(10) Patent No.: US 6,229,038 B1
(45) Date of Patent: May 8, 2001

(54) DICARBOXY ALKYL PHOSPHATE ESTERS

(75) Inventor: Anthony J. O'Lenick, Jr., Dacula, GA (US)

(73) Assignee: Applied Carbo Chemicals Inc., E. Lansing, MI (US)

(*) Notice: Subject to any disclaimer, the term of this patent is extended or adjusted under 35 U.S.C. 154(b) by 0 days.

(21) Appl. No.: 09/611,429

(22) Filed: Jul. 7, 2000

Related U.S. Application Data

(63) Continuation-in-part of application No. 09/493,172, filed on Jan. 28, 2000.

(51) Int. Cl.$^7$ .................................................. C07F 9/40
(52) U.S. Cl. .................................................. 558/180
(58) Field of Search ................................................ 558/180

(56) References Cited

U.S. PATENT DOCUMENTS 4,209,449   6/1980   Mayhew et al. .

*Primary Examiner*—Michael G. Ambrose

(57) ABSTRACT

The present invention relates to a (a) novel dicarboxy alkyl phosphate esters, (b) a method for the preparation of said phosphate ester and (c) application of said phosphate ester in industrial and personal care applications.

The compounds of the present invention are made by reacting epoxy succinic acid and a salt of an alkyl phosphate ester under aqueous conditions. The resulting compound is quite stable and offers excellent emulsification properties.

19 Claims, No Drawings

DICARBOXY ALKYL PHOSPHATE ESTERS

RELATED APPLICATION

This application is a continuation in part of copending application Ser. No. 09/493,172 filed Jan. 28, 2000.

BACKGROUND OF THE INVENTION

(1) Field of Invention

The present invention relates to a (a) novel dicarboxy phosphate ester, (b) a method for preparation of said dicarboxy phosphate ester and (c) application of said dicarboxy phosphate ester in industrial and personal care applications.

The compounds of the present invention are made by reacting epoxy succinic acid and a salt of an alkyl phosphate ester under aqueous conditions. The resulting compound is quite stable very mild to hair and skin and offers excellent surfactant properties, including detergency and foam. In addition, compounds of the present invention containing a pendant hydroxyl group which alters the water solubility and emulsification properties of the compound.

(2) Object of the Invention

It is the object of the present invention to provide novel compounds and a process for their preparation. These surface active agents that are well tolerated by skin and eyes. These non-irritating products produce copious foam, have outstanding emulsification properties and are ideal products for use in the formulation of hair and skin care products like shampoos, conditioners and body washes.

(3) Description of the Arts and Practices

U.S. Pat. No. 4,065,475 to Hosi et al issued in December of 1977 discloses a process for preparation of cis epoxy succinic acid, a raw material for the preparation of the compounds of the present invention. This material is easily made by the reaction of maleic acid with hydrogen peroxide in the presence of a tungsten catalyst. The availability of this high purity raw material is very critical in the preparation of the compounds of the present invention.

THE INVENTION

1) SUMMARY OF THE INVENTION

The compounds of the present invention are made by reacting cis epoxy succinic acid with a salt of an alkyl phosphate ester under aqueous conditions. The resulting compound is an outstanding surfactant for personal care applications.

DETAILED DESCRIPTION OF THE INVENTION

The compounds of the present invention have several key portions in the molecule. Those groups include (a) an alkyl phosphate group, (b) a hydroxy linkage group and (c) two carboxy groups that improve water solubility. These groups and their positioning in the molecule result in unique properties for the molecule. These include foam, detergency, chelation properties (especially for calcium ion), emulsification properties, wetting properties, particularly for hydrophobic pigments, and a lubricious skin feel. This combination of properties has heretofore been unattainable in one molecule.

Compounds of the invention conform to the following structure:

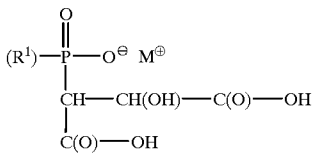

wherein;

$R^1$ is:

$CH_3(CH_2)_s-O-(CH_2CH_2-O)_z-(CH_2CH(CH_3)O)_y-(CH_2CH_2-O)_x-$;

s is an integer ranging from 3 to 21;

x, y and z are independently integers ranging from 0 to 20;

M is selected from the group consisting of H, Na, K, Li, and $NH_4$.

Illustrative of the sequence for the preparation of the compounds of the present is as follows;

In a 30% aqueous solution the disodium salt of a phosphate ester (pH 10.4) is reacted with an epoxy succinic acid to produce the phosphate ester of the present invention:

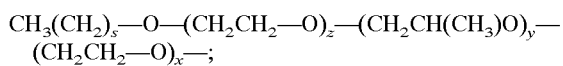

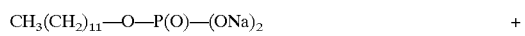

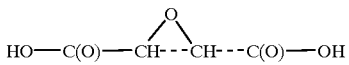

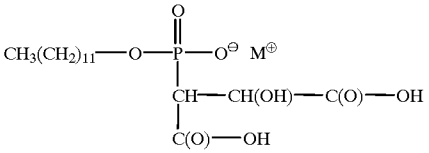

The compounds of the present invention are very good ingredients in a variety of applications due to the presence of both the phosphate and the two carboxyl groups. These applications include:

(a) emulsion polymerization;

(b) urethane foams as modifiers of bubble structure;

(c) pigment dispersion agents for hydrophobic pigments;

(d) personal care applications for excellent skin feel.

Preferred Embodiments

In a preferred embodiment s is 3.

In a preferred embodiment s is 5.

In a preferred embodiment s is 7.

In a preferred embodiment s is 9.

In a preferred embodiment s is 11.

In a preferred embodiment s is 13.

In a preferred embodiments is 16.

In a preferred embodiment x,y, and z are each zero.

In a preferred embodiment x ranges from 3 to 10.

In a preferred embodiment y ranges from 1 to 10.

In a preferred embodiment s is 11 and x ranges from 3 to 10.

In a preferred embodiment s is 13 and x ranges from 3 to 10.

In a preferred embodiment s is 15 and x ranges from 3 to 10.

EXAMPLES

RAW MATERIALS

Epoxy Succinic Acid

U.S. Pat. No. 4,065,475 to Hosi et al issued in December of 1977 discloses a process for preparation of cis epoxy succinic acid, a raw material for the preparation of the compounds of the present invention.

Epoxy succinic acid conforms to the following structure:

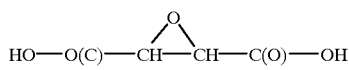

and is commercially available from a variety of sources.

Phosphate Esters

The phosphate esters useful as intermediates for the preparation of the compounds present invention are commercially available from Siltech LLC, Dacula Ga.

They conform to the following structure:

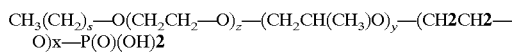

s is an integer ranging from 3 to 21;
and z are integers and are independently ranging from 0 to 20.

| Example | s | x | y | z |
|---|---|---|---|---|
| 1 | 3 | 0 | 0 | 0 |
| 2 | 5 | 0 | 0 | 0 |
| 3 | 7 | 0 | 0 | 0 |
| 4 | 9 | 0 | 0 | 0 |
| 5 | 11 | 0 | 0 | 10 |
| 6 | 17 | 0 | 0 | 10 |
| 7 | 3 | 0 | 0 | 0 |
| 8 | 5 | 10 | 1 | 20 |
| 9 | 9 | 15 | 20 | 5 |
| 10 | 11 | 20 | 3 | 10 |
| 11 | 17 | 20 | 20 | 20 |
| 12 | 21 | 1 | 10 | 20 |

PREPARATION OF THE PRODUCTS OF THE PRESENT INVENTION

General Procedure

Into a suitable vessel equipped with thermometer, agitation and heating capabilities is added the specified amount of water. Next the specified amount of phosphate ester is added under good agitation. The pH is adjusted to 10.3 with the specified base. The reaction mass is heated to 70–80° C. and the epoxy succinic is added over 1 hour. The exotherm is watched so that the temperature does not exceed 95° C. The pH is kept between 8–9 by addition of base. If that temperature is reached, cooling is applied and the addition suspended.

After the addition is complete the reaction mass is held at between 80–90° C. for four hours. During that time the % epoxide becomes vanishingly low.

Examples 13–24

Example 13

Into a suitable vessel equipped with thermometer, agitation and heating capabilities is added 500.0 grams of water. Next add 171.0 grams of phosphate ester (Example 1) under good agitation. The pH is adjusted to 10.3 with the KOH. The reaction mass is heated to 70–80° C. Next add 132.0 grams of epoxy succinic acid (example 1). Addition is made over a 1 hour time period. The exotherm is watched so that the temperature does not exceed 95° C.

After the addition is complete the reaction mass is held at between 80–90° C. for four hours. During that time the % epoxide becomes vanishingly low.

Example 14–24

Example 13 is repeated, only this time the specified amount of water is added, and the specified quantity and type of phosphate ester is added replacing the quantity and type in example 13.

| | Phosphate Ester | | Water | Base |
|---|---|---|---|---|
| Example | Example | Grams | Grams | Type |
| 13 | 1 | 171.0 | 250.0 | KOH |
| 14 | 2 | 199.0 | 400.0 | KOH |
| 15 | 3 | 227.0 | 500.0 | NaOH |
| 16 | 4 | 255.0 | 500.0 | NaOH |
| 17 | 5 | 723.0 | 1400.0 | KOH |
| 18 | 6 | 807.0 | 2000.0 | NaOH |
| 19 | 7 | 171.0 | 342.0 | KOH |
| 20 | 8 | 1578.0 | 3000.0 | KOH |
| 21 | 9 | 2315.0 | 5000.0 | KOH |
| 22 | 10 | 1780.0 | 3200.0 | KOH |
| 23 | 11 | 3307.0 | 6614.0 | NaOH |
| 24 | 12 | 2567.0 | 5000.0 | NaOH |
| 25 | 12 | 2567.0 | 5000.0 | NaOH |
| 26 | 11 | 3307.0 | 6700.0 | KOH |
| 27 | 10 | 1780.0 | 3200.0 | LiOH |
| 28 | 9 | 2315.0 | 3900.0 | KOH |
| 29 | 8 | 1578.0 | 7530.0 | NH$_4$OH |
| 30 | 1 | 171.0 | 250.0 | KOH |
| 31 | 2 | 199.0 | 400.0 | KOH |
| 32 | 3 | 227.0 | 500.0 | NaOH |
| 33 | 4 | 255.0 | 500.0 | NaOH |
| 34 | 5 | 723.0 | 1400.0 | KOH |
| 35 | 6 | 807.0 | 2000.0 | NaOH |

The compounds of the present invention are in aqueous solution or emulsion and generally range from 20–60% solids. The preferred range is 30–40% solids. The products are used without purification.

Applications

The products of the present invention are useful in:

(a) emulsion polymerization—The compounds are used at very low concentrations resulting in less water blush. A problem well known to those skilled in the emulsion polymer art.

(b) personal care applications (for excellent skin feel)—The products of the present invention have a very lubricious feel on the skin.

(c) Personal care applications (as detergents)—The compounds provide copious foam and are mild detergents. They do not sting and are non-irritation.

(d) personal cars applications (liposomes)—Finally, the compounds find applications in the formation of liquid crystals and liposomes in personal care applications.

What is claimed is:

1. A compound conforming to the following structure

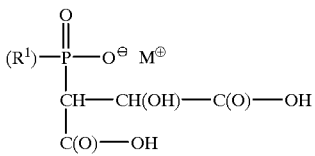

wherein;

R[1] is:

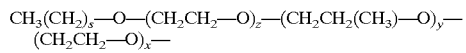

s is an integer ranging from 3 to 21;

x, y and z are independently integers ranging from 0 to 20;

M is selected from the group consisting of H, Na, K, Li, and $NH_4$.

2. A compound of claim 1 wherein s is 3.
3. A compound of claim 1 wherein s is 5.
4. A compound of claim 1 wherein s is 7.
5. A compound of claim 1 wherein s is 9.
6. A compound of claim 1 wherein s is 11.
7. A compound of claim 1 wherein s is 13.
8. A compound of claim 1 wherein s is 17.
9. A compound of claim 1 wherein s is 19.
10. A compound of claim 1 wherein s is 21.
11. A compound of claim 1 wherein x, y, and z are each zero.
12. A compound of claim 1 wherein x ranges from 3 to 10.
13. A compound of claim 1 wherein y ranges from 1 to 10.
14. A compound of claim 11 wherein s is 3.
15. A compound of claim 11 wherein s is 5.
16. A compound of claim 11 wherein s is 7.
17. A compound of claim 11 wherein s is 9.
18. A compound of claim 11 wherein s is 11.
19. A compound of claim 11 wherein s is 13.

* * * * *